United States Patent [19]
Pournoor et al.

[11] Patent Number: 5,308,180
[45] Date of Patent: May 3, 1994

[54] LIQUID APPLICATOR WITH METERING INSERT

[75] Inventors: Kaveh Pournoor; John D. Dell, both of St. Paul, Minn.

[73] Assignee: Minnesota Mining and Manufacturing Company, St. Paul, Minn.

[21] Appl. No.: 985,666

[22] Filed: Dec. 4, 1992

Related U.S. Application Data

[63] Continuation-in-part of Ser. No. 804,294, Dec. 9, 1991.

[51] Int. Cl.$^5$ .................... A47L 13/17; A61M 35/00
[52] U.S. Cl. .................................... 401/205; 401/132; 604/3
[58] Field of Search ............... 401/132, 133, 134, 135, 401/205; 604/2, 3

[56] References Cited

U.S. PATENT DOCUMENTS

| | | |
|---|---|---|
| 1,221,227 | 4/1917 | Schulz . |
| 2,345,080 | 3/1941 | Von Ardenne ........................ 164/85 |

(List continued on next page.)

FOREIGN PATENT DOCUMENTS

| | | |
|---|---|---|
| 87/107736 | 2/1987 | European Pat. Off. . |
| 292325 | 11/1988 | European Pat. Off. . |
| 327398 | 8/1989 | European Pat. Off. . |
| 0459893A1 | 12/1991 | European Pat. Off. . |
| 153904 | 7/1938 | Fed. Rep. of Germany ...... 401/133 |
| 2124298 | 11/1972 | Fed. Rep. of Germany ...... 401/133 |
| 2040140 | 9/1974 | Fed. Rep. of Germany . |
| 2541918 | 3/1977 | Fed. Rep. of Germany ...... 401/132 |
| 2719275 | 11/1977 | Fed. Rep. of Germany . |
| 3629601 | 3/1988 | Fed. Rep. of Germany . |
| 421408 | 5/1947 | Italy .................................... 401/132 |
| 6249094 | 7/1980 | Japan . |
| 4-12243 | 1/1992 | Japan . |
| 2190028A | 11/1987 | United Kingdom . |

OTHER PUBLICATIONS

Dyer, Jenkins, and Sidhu, *Development and Origin of Conical Structures on XeCl Laser Ablated Polyimide*, Applied Physics Lett., vol. 49, Iss. 8, pp. 453–455, 1986.
Mai, Moshrefzadeh, Gibson, Stegeman, and Seaton, (List continued on next page.)

"Simple Versatile Method for Fabricating Guided--Wave Gratings", *Applied Optics*, vol. 24, No. 19, 1985.
"A Fast, Easy, Long-Lasting I.V. Prep That Can Help Enhance Dressing Adhesion," Medical-Surgical Division, 3M Health Care, 3M Center, St. Paul, Minn., 1989 (Brochure).
"Duraprep TM Solution—Now Ideal for Outpatient, Office-Based and Other Minor Surgical Procedures," Medical-Surgical Products, 3M Health Care, 3M Center, St. Paul, Minn., 1991 (Brochure).
"Obsoletely? Absolutely!," Medical-Surgical Division, 3M Health Care Group, 3M Center, St. Paul, Minn., Mar. 1988 (Brochure).
Hollen, N. et al., *Textiles*, Iowa State University, 1968, pp. 118–119.
R. Srinivasan et al., "Ultraviolet Laser Ablation of Organic Polymers," *Chem. Rev.*, 1989, pp. 1303–1316.
W. Ehrfeld et al., "Progress in deep-etch synchrotron radiation lithography," *J. Vac. Sci. Technol.*, B6(1), Jan.-/Feb. 1988, pp. 178–182.
W. Ehrfeld et al., "Microfabrication of Membranes With Extreme Porosity And Uniform Pore Size," *Journal of Membrane Science*, 36 (1988), pp. 67–77.
R. Woodin et al., "Lasers in Chemical Processing," *C&EN*, Dec. 17, 1990, pp. 20–31.
F. Schellenberg et al., "Photosensitized Polystyrene As A High Efficiency Relief Hologram Medium," *SPIE*, vol. 1051 Practical Holography III (1989), pp. 31–43.

*Primary Examiner*—Steven A. Bratlie
*Attorney, Agent, or Firm*—Gary L. Griswold; Walter N. Kirn; Jennie G. Boeder

[57] ABSTRACT

A liquid applicator is provided which is particularly useful in applying preoperative surgical scrubs or paints to skin. The article is provided with an inner layer of flexible porous material and an outer layer of open cell foam sponge material. The flexible, porous layer regulates the flow of liquid therethrough to provide acceptable wetting of the foam sponge while preventing dripping therefrom. The applicator includes a means of maintaining atmospheric pressure within the applicator while the liquid is being dispersed.

12 Claims, 7 Drawing Sheets

OTHER PUBLICATIONS

| Patent No. | Date | Name | Class |
|---|---|---|---|
| 2,853,727 | 9/1958 | Nadai . | |
| 2,926,104 | 2/1960 | Goetz | 117/65 |
| 3,073,303 | 1/1963 | Schaar | 128/156 |
| 3,087,463 | 4/1963 | Kahn et al. | 401/135 |
| 3,132,370 | 5/1964 | Capezzuto . | |
| 3,303,085 | 2/1962 | Price et al. | 161/109 |
| 3,393,962 | 7/1968 | Andrews | 401/132 |
| 3,393,963 | 7/1968 | Nadai . | |
| 3,422,246 | 1/1969 | Wetzel | 219/121 |
| 3,479,122 | 11/1969 | Funahashi | 401/132 X |
| 3,612,871 | 10/1971 | Crawford et al. | 250/83 |
| 3,617,702 | 11/1971 | Flournoy | 219/384 |
| 4,032,743 | 6/1977 | Erbach et al. | 219/121 LM |
| 4,044,222 | 8/1977 | Kestenbaum | 219/121 LM |
| 4,053,243 | 10/1977 | Levin | 401/133 X |
| 4,092,515 | 5/1978 | Joslin et al. | 219/121 LM |
| 4,128,752 | 12/1978 | Gravel | 219/121 L |
| 4,141,838 | 2/1979 | Schilling | 210/498 |
| 4,183,684 | 1/1980 | Avery, Jr. | 401/133 |
| 4,262,186 | 4/1981 | Provancher | 219/121 LH |
| 4,297,559 | 10/1981 | Whitman, III | 219/121 LB |
| 4,342,522 | 8/1982 | Mackles . | |
| 4,356,375 | 10/1982 | Josephy et al. | 219/121 LH |
| 4,374,314 | 2/1983 | Deacutis | 219/121 LJ |
| 4,379,022 | 4/1983 | Melcher et al. | 156/643 |
| 4,402,571 | 9/1983 | Cowan et al. | 350/162.17 |
| 4,415,288 | 11/1983 | Gordon et al. . | |
| 4,496,216 | 1/1985 | Cowan | 350/162.17 |
| 4,498,796 | 2/1985 | Gordon et al. . | |
| 4,507,111 | 3/1985 | Gordon et al. . | |
| 4,542,012 | 9/1985 | Dell . | |
| 4,568,815 | 2/1986 | Kimbara et al. | 219/121 LK |
| 4,572,689 | 2/1986 | Chernack . | |
| 4,584,192 | 4/1986 | Dell et al. . | |
| 4,588,319 | 5/1986 | Niemeyer | 401/205 |
| 4,608,968 | 9/1986 | Rosofsky . | |
| 4,633,058 | 12/1986 | Jones | 219/121 LK |
| 4,652,412 | 3/1987 | Chiulli | 264/49 |
| 4,661,212 | 4/1987 | Ehrfeld et al. | 204/11 |
| 4,661,565 | 4/1987 | Noding | 525/437 |
| 4,690,750 | 9/1987 | Roxlo et al. | 208/310 Z |
| 4,699,637 | 10/1987 | Iniotakis et al. | 55/158 |
| 4,714,516 | 12/1987 | Eichelberger et al. | 156/628 |
| 4,734,558 | 3/1988 | Nakano et al. | 219/121 LP |
| 4,797,211 | 1/1989 | Ehrfeld et al. | 210/321.84 |
| 4,803,337 | 2/1989 | Ishikawa et al. | 219/121.85 |
| 4,855,049 | 8/1989 | Toulemonde et al. | 210/500.40 |
| 4,923,608 | 5/1990 | Flottman et al. | 210/500.25 |
| 4,925,327 | 5/1990 | Wirt | 401/132 X |
| 4,957,385 | 9/1990 | Weinstein | 604/3 X |
| 5,098,297 | 3/1992 | Chari et al. | 401/132 X |

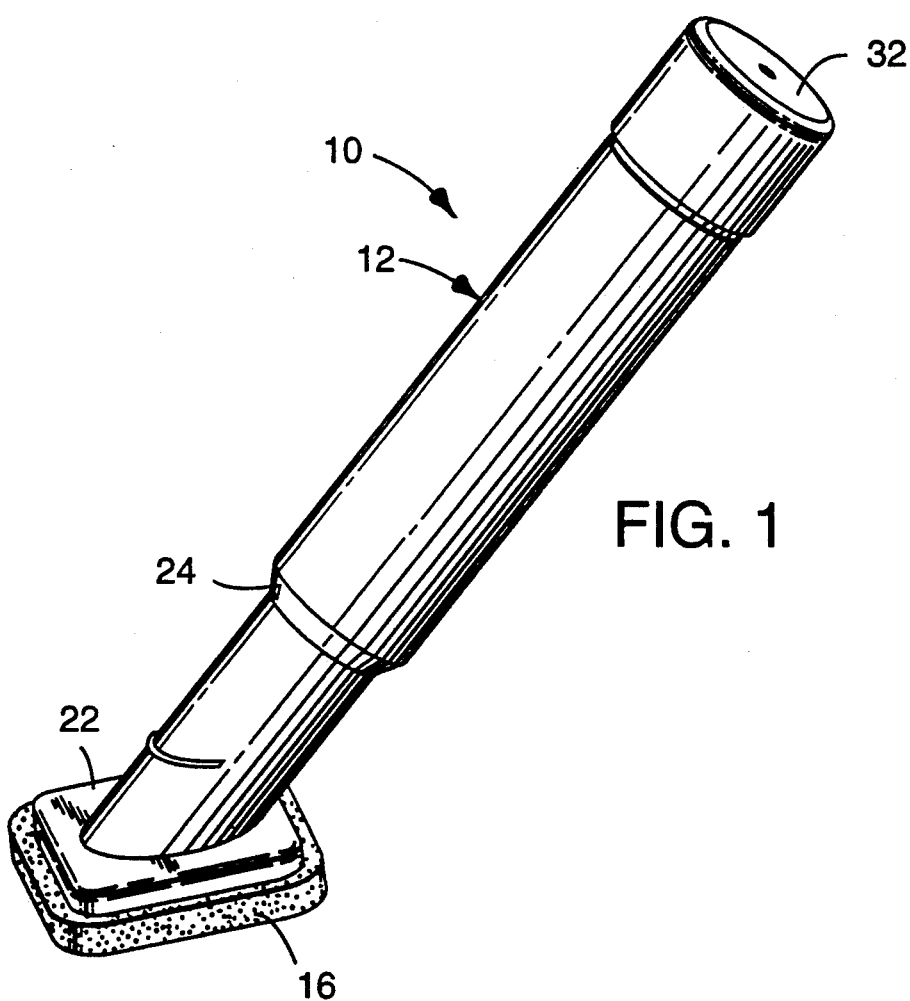

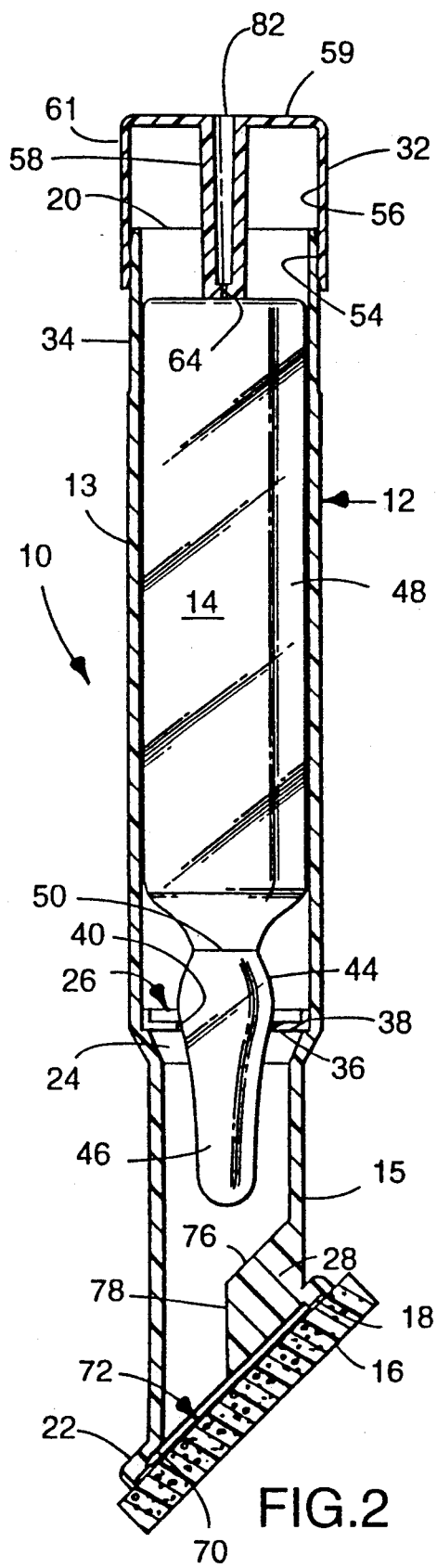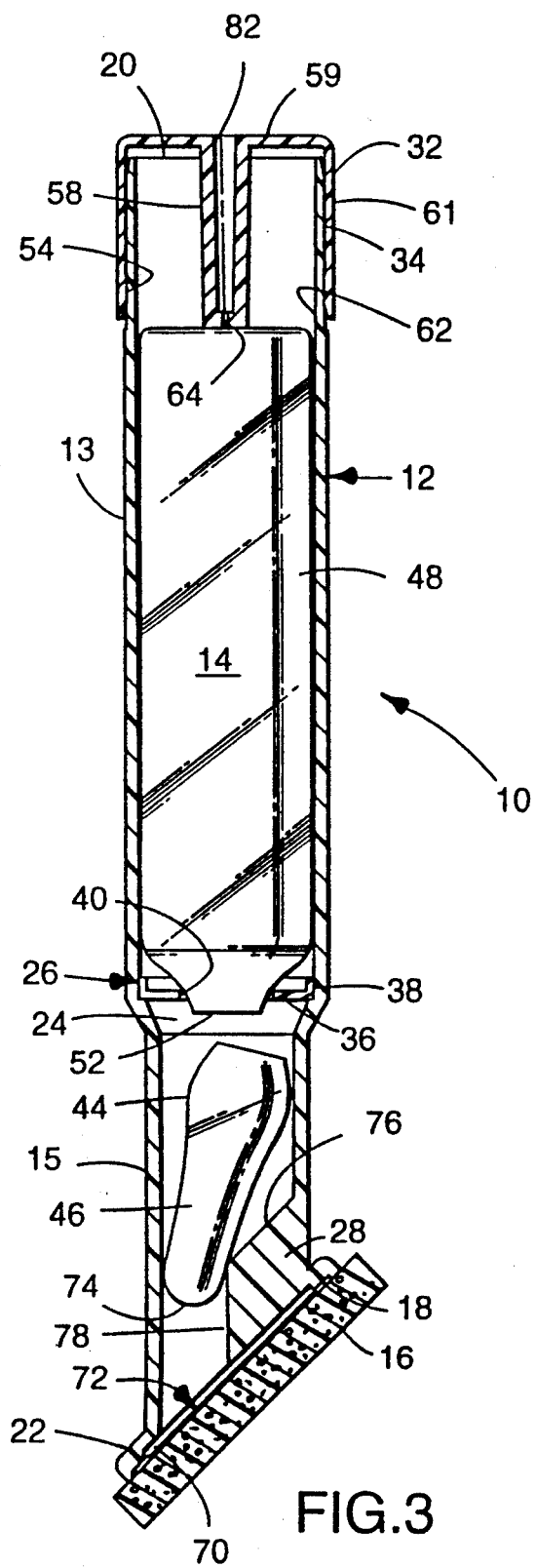

LIQUID APPLICATOR WITH METERING INSERT

This is a continuation in part of application Ser. No. 804,294, filed Dec. 9, 1991.

TECHNICAL FIELD

This invention relates to liquid applicators having particular utility in the field of surgery preparation. Most particularly, this invention relates to articles useful in applying pre operative surgical scrubs or paints to skin.

BACKGROUND OF THE INVENTION

Antiseptic preparation of patients for surgery conventionally includes a 3-10 minute scrubbing of the affected area with a soap solution followed by the application of a water soluble antiseptic paint solution. These solutions are generally applied with saturated sponges that are attached to a blade or held with forceps. The sponges are saturated by soaking in open pans of solution. Numerous devices have been developed in an attempt to prevent the dripping of solution associated with the original technique. Another goal was to reduce the time required for application of the antiseptic solution.

An important problem associated with the original prior art devices developed to apply surgical prep solutions was the lack of control of the delivery of the liquid to the sponge in a manner that prevented dripping. Additional problems encountered with such devices include reliability of rupturable surfaces, manufacturing complexity and inappropriate geometries.

U.S. Pat. Nos. 4,415,288; 4,507,111; and 4,498,796 describe surgical scrub devices that include a liquid containing, rupturable, cylindrical cartridge which is slidable within a tubular handle having one or two longitudinally oriented hollow spikes that communicate to recesses in the interior of a sponge. Sliding the cartridge in the tubular handle causes the spikes to rupture one end of the cartridge. Liquid from the cartridge flows through the lumen of the spikes to the sponge. Liquid can flow through the spikes by gravity or by application of external pressure by deforming a flexible handle and cartridge. In order for liquid to flow by gravity from this device, air must be entrained into the cartridge through the sponge and at least one hollow spike. For the following two reasons, this is not a reliable and predictable means to control the rate of delivery of liquid to the sponge. First, as the sponge becomes wet its air permeability decreases thereby restricting the entrainment of air. Second, hollow tubes with sufficiently small inside diameters to effectively meter the liquid flow rate to prevent dripping tend to "air lock" due to the surface tension of the liquid. Although external pressure can be applied to a flexible device, in practice it is very difficult to deliver precisely the correct volume of liquid to saturate the sponge without dripping.

U.S. Pat. No. 4,342,522 describes a roll on dispenser which includes a porous open cell foam membrane deformable by an applicator ball to regulate the dispensation of controlled amounts of powders. The amount of material dispensed is dependent upon the porosity of the membrane which is dependent upon the degree of deformation of the membrane by the ball upon operation of the dispenser.

U.S. Pat. No. 3,393,963 discloses a dispenser for liquids which has particular utility in applying deodorants, perfumes, liquid lipsticks and the like. The device includes a container holding a supply of liquid, a reservoir body mounted on the outlet of the container and an applicator membrane mounted over, but spaced apart, from the reservoir member. Both the reservoir body and the membrane are made from elastic, porous, preferably foamed material. In use, the dispenser is shaken so as to cause liquid to flow into the porous reservoir member. The porous membrane is then pressed against the skin of the body, causing it to contact the upper surface of the porous reservoir body so that liquid contained therein is pressed through the porous membrane for application to the skin. The amount of liquid to be applied to the skin is regulated by pressure exerted during application of the liquid.

U.S. Pat. No. 4,183,684 describes a fluid dispenser that includes a liquid-containing ampoule in a flexible housing. A porous pad element which may include a gauze like layer and a sponge layer is disposed over the bottom opening. The liquid is released to the porous pad by crushing the ampoule through the flexible housing walls.

Coassigned U.S. Pat. No. 4,925,327, which is hereby incorporated by reference, describes a liquid applicator which incorporates a rigid, porous metering insert to regulate the flow rate of liquid into a sponge. The metering insert is disposed between the applicator handle and a foam sponge covering the major orifice of the handle. The applicator handle incorporates a vent to entrain air into the applicator as liquid flows through the metering element into the sponge. A bonding insert comprised of a thermoplastic or heat activatable material filled with an inductively active material is adapted to bond the applicator handle, metering insert and sponge together. This applicator, while an improvement over the art due to its dripless nature, employs a relatively expensive porous metering insert which is difficult to manufacture so as to provide reproduceable units.

SUMMARY OF THE INVENTION

This invention relates to an article useful as a dispenser for the application of a liquid to a surface comprising
(a) a hollow elongate member having a first major orifice at one end thereof;
(b) a flexible, porous layer disposed over the first major orifice having at least one array of pores extending therein, each array of pores having an average pore size of between about 1 and 100 microns and a distribution of pore sizes of less than about 30 percent of the average pore size;
(c) a layer of sponge material disposed over the exterior surface of the porous layer; and
(d) means of maintaining atmospheric pressure within the hollow elongate member while the liquid to be applied by the applicator is being dispensed.

The invention provides a means to reliably deliver in a short period of time a surgical prep solution to an applicator sponge without dripping. The applicator of the present invention controls the flow rate of liquid therein to the applicator sponge without the need for external operator manipulation such as squeezing the liquid container or compressing the applicator sponge against an external surface.

In a preferred embodiment of the applicator of the invention the flexible porous layer is a microstructured membrane comprising a sheet having a first major face and a second major face with at least one array of pores extending through the sheet, each array of pores having an average characteristic dimension of between about 1 and about 100 microns and a pore size distribution of less than about 10 percent. Such microstructured membranes provide improved reproduceability of average flow rate for liquids being dispensed.

In a preferred embodiment the applicator further includes
(e) deformable means contained within the hollow elongate member for supporting and protecting a reservoir container containing the liquid to be dispensed, the deformable means having an aperture through which at least a portion of the reservoir container may be pushed;
(f) means for limiting the axial displacement of the deformable means while at least a portion of the container is pushed through the aperture in the deformable means; and
(g) means associated with the hollow elongate member for rupturing the reservoir container after at least a portion of the container is pushed through the aperture in the deformable means.

Although this preferred device can be easily actuated by the application of a small steady force to push the reservoir container through the deformable means and into contact with the rupturing means, the liquid filled rupturable container is protected from breakage from large impact forces which may occur during shipping or handling. Although intended to apply modern, low viscosity, non water soluble, film forming prep solutions, this device can be configured to apply a variety of solution compositions, viscosities, densities and volumes without compromising the fast wetting and no dripping features.

BRIEF DESCRIPTION OF THE DRAWINGS

A more complete understanding of the invention and its advantages will be apparent from the Detailed Description taken in conjunction with the accompanying Drawings, in which:

FIG. 1 is a perspective view of a preferred applicator of this invention;

FIG. 2 is a cross section side view of the preferred applicator showing the rupturable reservoir container supported and intact, as for shipping;

FIG. 3 is a cross section side view similar to that of FIG. 2, except that the reservoir container has been broken by a user in order to charge the applicator for use;

DETAILED DESCRIPTION

Figure 2A:
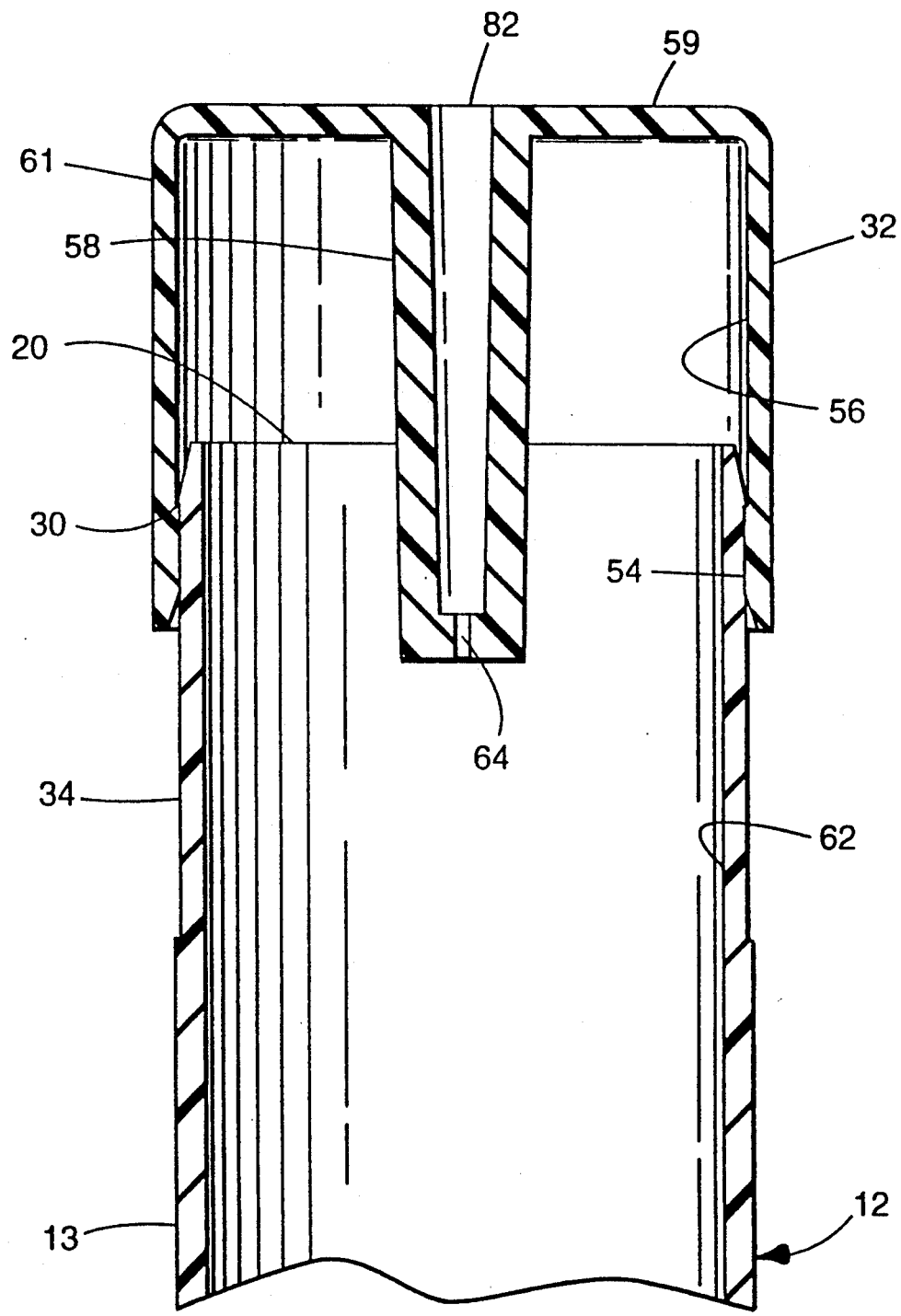
FIG. 2A is an enlargement of the second orifice of the hollow elongate member and the cap of the applicator of FIG. 1.

With reference to the embodiment depicted in FIGS. 1 through 6, the applicator 10 includes a hollow elongate member 12 adapted to support and protect a rupturable reservoir container in the form of a frangible ampoule 14 containing the solution to be applied by the applicator 10. The hollow elongate member 12 acts as a handle and as a fluid container after the ampoule 14 has been broken, but before the solution is dispensed by the foam sponge 16. The hollow elongate member 12 is bounded by a first major orifice 18 and second major orifice 20, one at each end. A flange 22 adapted to accept the flexible, porous layer 66 and foam sponge 16 surrounds the first major orifice 18.

Figure 4:
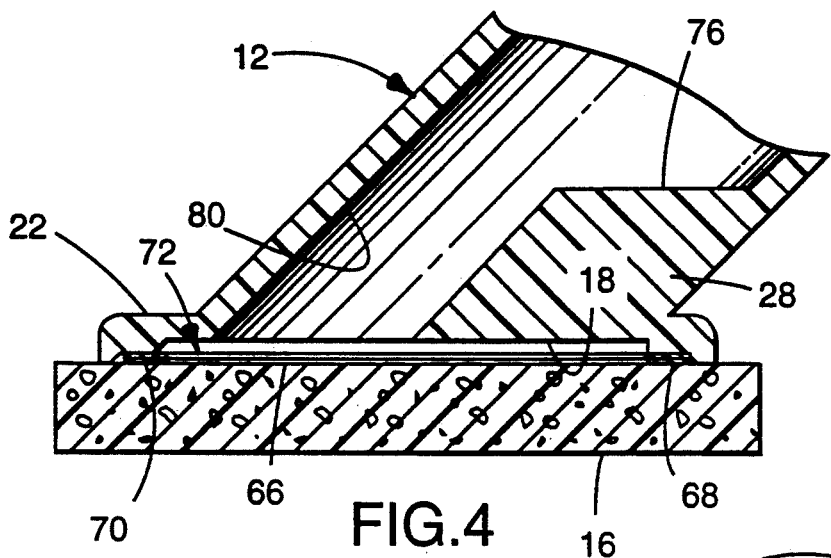
FIG. 4 is a cross section detail view of the dispensing end of the applicator of FIG. 1.
Figure 5:
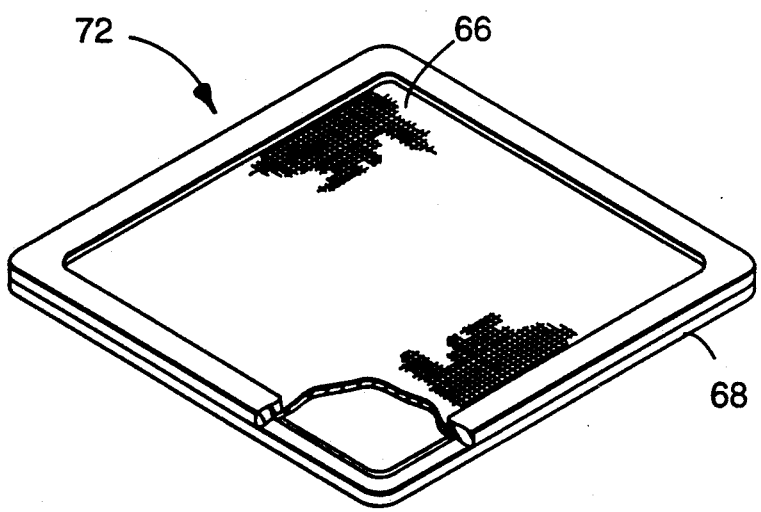
FIG. 5 is a perspective view of a preferred flexible, porous layer in a rigid frame.

Referring now to FIGS. 4 and 5, a flexible, porous layer 66 of porous material incorporated in a structurally rigid frame 68 is disposed over the first major orifice 18 of the hollow elongate member 12, and is sandwiched between the flange 22 and the foam sponge 16. The porous layer 66 is disposed over the first major orifice 18 to control the flow of liquid out of the hollow elongate member 12 and into the foam sponge 16.

In a preferred embodiment, the hollow elongate member 12 is conveniently constructed to include a shoulder 24 for retaining a collar 26, which serves as a preferred deformable means for supporting and protecting the ampoule 14 until the applicator 10 is to be used. A wedge 28 is conveniently constructed adjacent to the first major orifice which serves as a means for breaking the ampoule 14.

Figure 6:
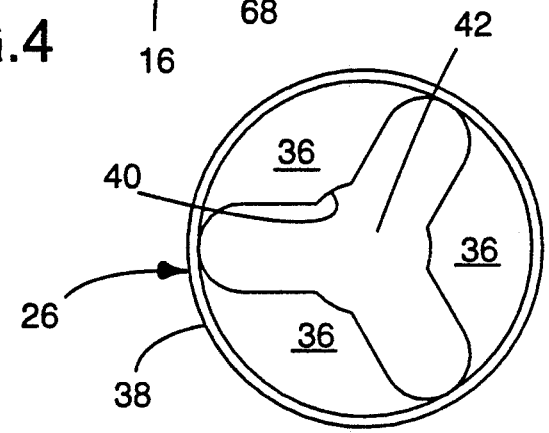
FIG. 6 is a plan view of a deformable means for supporting the rupturable reservoir container.

Referring particularly to FIG. 6, the collar 26 is conveniently constructed to include a plurality of radially projecting, cantilevered beam elements 36 projecting at a substantially right angle from annular rim 38. In particularly preferred embodiments, the inside edge 40 of each of the beam elements 36 is curved, and together these curves define a central aperture 42. This aperture is specifically adapted to engage the bulb 44 of the neck portion 46 of the ampoule 14.

In the embodiment depicted, the collar 26 is disposed between the first 18 and second 20 major orifices of the hollow elongate member 12 at a position that is conveniently determined by shoulder 24. Prior to actuation, the collar 26 prevents the neck portion 46 of the ampoule 14 from contacting the wedge 28. During actuation of the applicator 10, the bulb 44 of the ampoule 14 is pushed through the collar 26, causing the neck portion 46 to contact the wedge 28. The wedge 28 exerts a force perpendicular to the axis of the neck portion 46 of the ampoule 14 that results in the separation of the neck portion 46 from the body portion 48 of the ampoule 14. This separation is facilitated by a stress concentrator 50 between the neck portion 46 and body portion 48.

Referring to FIG. 3, after the separation, the collar 26 acts to axially separate the neck portion 46 from the body portion 48, facilitating the flow of liquid from the ampoule 14. If the neck portion 46 were to remain in close proximity to the ampoule body 48, the opening formed by the rupturing of the stress concentrator 50 for the liquid to escape the ampoule 14 could be restricted.

The cap 32 is adapted to close the second major orifice 20 of the hollow elongate member 12 after insertion of the ampoule 14 during assembly of the applicator 10. The cap 32 is constructed to transmit the actuation force to the ampoule 14, vent the interior of the applicator to prevent "air locking" and provide a leakproof seal. The cap 32 is axially retained to the hollow elongate member 12 by a snap fit joint created by the internally projecting lip 54 of the cap 32 and the externally projecting ridge 30 of the hollow elongate member 12. The cap 32 is constructed to include an axially projecting column 58 from the interior surface. The column 58 contains an axial hole that vents the interior of the applicator 10 to maintain atmospheric pressure as liquid flows out through the first orifice 18 of the hollow elongate member 12 into the foam sponge 16.

The foam sponge 16 can be selected from a variety of commercially available materials having a wide range of compression set ratios, densities and porosities. By varying the pore size, pore size distribution, void volume fraction and surface energy of the porous material in the metering/bonding insert and the compression set ratio and porosity of the foam sponge, applicators can be constructed to apply a variety of solution compositions, viscosities, densities and volumes. The pore size, pore size distribution, void volume fraction and surface energy of the porous material in the metering/bonding insert and the compression set ratio and porosity of the open cell foam sponge are adjusted in relation to the viscosity, density, volume and surface tension of the liquid to be dispensed to allow a portion of the liquid contained in the applicator to flow to the outer surface of the foam sponge without dripping when the applicator is suspended with the flange down. It should be noted that to create a completely dripless applicator, the amount of liquid to be dispensed by the device must not exceed the reservoiring capacity of the foam sponge.

The invention will now be more particularly described in terms of the following particularly preferred embodiment. Referring to FIGS. 1-3, the applicator 10 consists of the following components: a frangible ampoule 14 containing the solution to be dispensed; a hollow elongate member 12 adapted to accept the ampoule 14, and having a flange 22 surrounding a first orifice 18; a collar 26 disposed within the hollow elongate member 12; a cap 32 including an air vent 64 positioned over the second major orifice 20 of the hollow elongate member 12; an integral metering/bonding insert 72 disposed within the flange 22 of the hollow elongate member 12; and a foam sponge 16 disposed over the metering/bonding insert 72.

The frangible ampoule 14 is preferably made of glass, with a stress concentrator 50 at a constriction separating a neck portion 46 from the body portion 48 of the ampoule 14. The neck portion 46 of the ampoule 14 includes a bulb 44 disposed between the lower end 74 of the neck portion 46 and the stress concentrator 50 of the ampoule. Frangible ampoules such as this are well known in the pharmaceutical field.

The hollow elongate member 12 can be molded from any thermoplastic material compatible with the liquid to be dispensed. Preferably, the hollow elongate member 12 is molded from high density polyethylene. Features of the preferred embodiment of this component include a tubular handle portion 13, a dispensing portion 15, a first major orifice 18 with a flange 22 which is integrally formed radially projecting and adapted to accept the metering/bonding insert 72, a wedge 28 adjacent to the first orifice 18, a second major orifice 20 with a surrounding ridge 30 on the exterior surface of the hollow elongate member adapted to retain a cap 32, and a shoulder 24 disposed between the first orifice 18 and second major orifice 20 adapted to support a collar 26.

For surgical prep applications, it is important that the hollow elongate member 12 be long enough to prevent contact of the patient by the person applying the surgical prep solution. Preferably, for such applications the hollow elongate member is at least four inches long. In the preferred embodiment, the tubular handle portion 13 of the hollow elongate member has a larger diameter to accommodate the body of the ampoule, than the dispensing portion 15 which accommodates the neck portion 46 of the ampoule.

Integrally formed flange 22 surrounds the first orifice 18 and is angled from the longitudinal axis of the hollow elongate member 12 by between 30 and 90 degrees. Most preferably, there is about a 45 degree angle between the flange 22 and the longitudinal axis of the hollow elongate member 12. The flange 22 preferably includes a recess 70 on the its interior surface. The recess is dimensioned and shaped to permit nesting therein of the metering/bonding insert 72.

Wedge 28 is positioned to extend within the dispensing portion 15 of the hollow elongate member 12 near the first orifice so as to be capable of contacting the end 74 of the neck portion 46 when the applicator 10 is actuated. Many different geometries are possible for the wedge 28. The preferred embodiment includes an integrally formed projection with a first edge 76 at an angle from the longitudinal axis of the hollow elongate member 12 of 30 to 60 degrees, most preferably about 45 degrees, and a second edge 78 parallel to the longitudinal axis. When the bulb 44 of ampoule 14 is pushed through the opening in collar 26 and towards the first orifice 18 of the hollow elongate member 12, the first edge 76 of the wedge 28 exerts a force perpendicular to the axis of hollow elongate member 12 on the neck portion 46 which ruptures ampoule 14 at the stress concentrator 50. The neck portion 46 is wedged between the second edge 78 of the wedge 28 and the interior wall 80 of the tubular handle 13 opposite the wedge 28. Many geometric variations of wedge 28 capable of exerting such a perpendicular force on the neck portion 46 when the ampoule 14 is displaced will occur to the skilled artisan.

The hollow elongate member 12 has an internal diameter transition between the tubular handle portion 13 and the dispensing portion 15 which provides shoulder 24 which is inwardly projecting and limits the axial displacement of a collar 26. Collar 26 serves as the deformable means which support ampoule 14 and prevents unintentional breakage of the ampoule due to impact forces during shipment and storage. The collar 26 is conveniently constructed from a thermoplastic material. In the preferred embodiment, the collar 26 is injection molded from high density polyethylene. Most preferably, the beam elements 36 of collar 26 project from the one edge of annular rim 38. The inside edges 40 of the radially projecting beam elements define a central aperture 42. The central aperture 42 is nominally the same diameter as the lower end 74 of the ampoule but significantly smaller than the diameter of the ampoule bulb 44. During assembly of the applicator 10, the collar 26 is inserted annular rim 38 up through second major orifice 20 into the hollow elongate member 12 to the level of the shoulder 24. Annular rim 38 lies adjacent shoulder 24, with its outer surface abutting handle portion 13 of the hollow elongate member just above the shoulder portion around the entire perimeter of the annular rim. Ampoule 14 is inserted in the hollow elongate member, lower end 74 first. The neck portion 46 partially projects through the collar 26; however, the central aperture 42 in the collar 26 is dimensioned such that in the assembled applicator, the bulb 44 of the neck portion 46 is not completely through the central aperture 42. The beam elements 36 exert a spring force on the bulb 44 and prevent the lower end 74 of the ampoule from contacting the wedge 28. The beam elements 36 dissipate impact or shock forces on the ampoule 14 that might occur during shipping. When the applicator is actuated, the beam elements 36 and annular rim 38 elastically and plastically deflect as the ampoule bulb 44 is pushed through the collar 26 and into contact with wedge 28.

In the preferred embodiment, the beam elements 36 are cantilevered from a thin annular rim 38. The annular rim 38 is designed to deflect when the beam elements 36 exert a critical bending moment upon it. This deflection of the rim effectively reduces the spring constant of the beam elements which produces a substantially constant force upon ampoule bulb 44 being forced through the central aperture 42 that is independent of ampoule bulb diameter. Without this effect, the force required to push an ampoule through the central aperture 42 in collar 26 would be nonlinearly related to the diameter of the ampoule bulb 44. Because glass ampoules of the type incorporated in this applicator are not manufactured by a blow molding process, the diameter of the bulb 44 of the ampoule 14 is significantly variable. Thus, without the use of the collar described herein, the force required to actuate each applicator would vary with each ampoule containing liquid to be dispensed. Preferably, the collar 26 is adapted to withstand the application of 13 to 18 Newtons of force without sufficient deflection to allow the ampoule bulb 44 to pass through central aperture 42, but deflects to allow the ampoule bulb to pass through the aperture upon application of at least about 22 Newtons of force.

In the preferred embodiment, a cap 32 covers the second major orifice 20 of the hollow elongate member 12. The cap includes an end wall 59 and annular side walls 61. The cap 32 can be fabricated from any compatible thermoplastic material. In the preferred embodiment, the cap element is injection molded from high density polyethylene. The cap is adapted to be attached to hollow elongate member 12 by means of a snap fit. This is accomplished by providing lip 54 inwardly projecting from side walls 61 adjacent to the major orifice 56 of the cap 32 which has a smaller inside diameter than the outside diameter of the outwardly projecting ridge 30 adjacent to the second major orifice 20 of the hollow elongate member 12. When the applicator 10 is assembled, the lip 54 of cap 32 is snapped over the outwardly projecting ridge 30 on the hollow elongate member 12. The cap 32 is also adapted to provide a liquid seal between the cap 32 and the hollow elongate member 12. This is accomplished by providing that the inside diameter of the inwardly projecting lip 54 on the cap 32 is smaller than the outside diameter of the sealing surface 34 of the hollow elongate member 12 thereby providing an axially slidable seal by means of an interference fit.

The cap 32 is adapted to transmit an actuation force to the ampoule 14 as the cap is axially displaced in the direction towards sponge 16. This force is transmitted by column 58 which axially projects from the interior surface of the end wall 59 of cap 32. Axial movement of column 58 in the direction towards sponge 16 forces the entire neck 46 of ampoule 14 through the central aperture 42 in collar 26 and causes the ampoule neck 46 to contact the wedge 28. In order to avoid creating a vacuum and restricting flow through the applicator, a means of maintaining atmospheric pressure in the device is preferably employed. Thus, in the preferred embodiment illustrated, column 58 is constructed with an axial hole with a first larger orifice 82 that communicates to the external surface of the cap, and an air vent 64 at the end of the column 58. The axial hole in the cap 32 functions to aspirate air into the internal volume of the applicator as the liquid flows into the foam sponge 16 to maintain atmospheric pressure within the device and prevent "air locking." Of course, other air vent means are envisioned by the inventors. Preferably, the geometry and location of the air vent would not result in leakage of liquid from the device. The annular volume between the end wall 59 and column 58 of the cap 32 and the inside surface 62 of the hollow elongate member 12 adjacent to the second major orifice 20 provides a reservoir for liquid when the applicator 10 is inverted. The height of column 58 is designed to always exceed the level of liquid in the annular volume thereby preventing liquid from leaking out of the air vent 64 of the column 58.

Referring to FIGS. 4 and 5, metering/bonding insert 72 which is dimensioned to rest in recess 70 of flange 22, includes a flexible, porous layer 66 of porous material surrounded by a substantially rigid frame 68, preferably fabricated from thermoplastic material. The metering/bonding insert 72 can be fabricated by attaching the porous layer 66 to separate rigid frame 68 by means of adhesives, thermal staking, ultrasonic bonding and other methods. Rigid frame 68 can be fabricated by injection molding, extrusion and die cutting. In the preferred embodiment the metering/bonding insert 72 is fabricated by injection insert molding a thermoplastic rigid frame 68 around the porous layer 66. Preferably, rigid frame 68 is comprised of a thermoplastic or heat activatable material filled with an inductively active material. Preferred examples include thermoplastic or heat-activatable material, such as polyethylene or hot melt adhesive, filled with an inductive metal or metal oxide powder, e.g., 5 to 50 percent by volume iron powder having an average particle size of about 300 to 400 mesh. A particularly preferred material is polyethylene filled with iron powder, commercially available from Ashland Chemical, Inc., Norwood, N.J., as "EMAWELD ® Resin G10-214". During assembly of the applicator 10, the metering/bonding insert 72 is sandwiched between the flange 22 surrounding the first orifice 18 of the hollow elongate member 12 and the foam sponge 16. The assembled applicator 10 is then held in an inductively inactive fixture, e.g., plastic, and exposed to a high frequency alternating electromagnetic field. The frame 68 of the metering/bonding insert 72 is inductively melted thereby bonding the hollow elongate member 12, the metering/bonding insert 72, and foam sponge 16 together.

The distribution and rate of delivery of the liquid to the open cell foam sponge 16 is controlled by the porous layer 66 incorporated in the integral metering/bonding insert 72. For a given volume, viscosity, density and surface tension of the liquid, wetting of the foam sponge without dripping can be accomplished by appropriate specification of the average pore size, pore size distribution, void volume fraction and surface energy of the material from which the porous layer 66 is formed, and the permanent compression set ratio and porosity of the foam sponge 16.

Preferably, the pore size, pore size distribution, void volume fraction and surface energy of the porous layer 66 incorporated in the metering/bonding insert 72 are adjusted so that for any given volume, viscosity, density and surface tension of the liquid to be applied the average flow rate of the liquid through the porous layer is between about 0.1 and 15 ml/sec. Greater flow rates than this will tend to result in an applicator which drips and applies uneven coats, while lower flow rates will result in an applicator which does not provide adequate liquid for surgical scrub applications. Most preferably, for surgical scrub applications the average flow rate of liquid through the porous layer 66 is between 0.25 and 10 ml/sec. In general, for lower volumes and/or higher viscosity liquids the pore size and/or void volume of the porous layer is adjusted upwards to achieve the desired flow rates.

The rigidity provided by the structural frame 68 of the metering/bonding insert 72 enables flexible porous materials to be utilized as the porous layer 66 that would otherwise be difficult to handle in manufacturing. The structural frame 68 permits the use of inexpensive porous materials manufactured as sheets as the porous layer 66 to control the liquid flow rate. Combining the inductively meltable frame 68 with the porous layer 66 reduces the manufacturing cost of the applicator by allowing the utilization of inexpensive porous material and by reducing the number of parts. Insert molding an inductively meltable frame 68 around the flexible porous layer 66 results in a single part that can be easily handled by automated production equipment.

The flexible porous layer in the metering/bonding element 72 is preferably a flexible fabric, porous film or porous membrane, such as porous plastic film or porous metal foil, and flexible nonwoven porous material. Useful fabrics may be woven, non-woven or knit. By flexible it is meant that the material from which the porous layer is made can be wrapped around a 1 millimeter diameter mandrel without breaking. In general, the average pore size of the porous layer is between about 1 and 100 microns and the void volume fraction is between about 0.5 and 50 percent. Preferably, for surgical applications where antiseptic solutions are dispensed, the average pore size of the porous layer is between 3 and 65 microns and the void volume fraction is between about 1 and 35 percent. Most preferably, for such applications the average pore size is between about 5 and 50 microns and the void volume is between about 2 and 20 percent. The distribution of the pore sizes are preferably less than about 30 percent of the average pore size, more preferably less than about 20 percent, and most preferably less than about 10 percent of the average pore size. Illustrative examples of materials which may be used to make the flexible porous layer useful in the practice of the invention include: polyvinyls such as acrylics and methacrylics, polyynes, polyenes (e.g., polyethylene, polypropylene, and polystyrene, polydienes (e.g., polybutadiene and polyisoprene), polyesters (e.g., terephphalate esters, etc.), polyurethanes, polyamides (e.g., nylons), polyimides, polyethers, polyacrylamides, polyacrylonitriles, polycarbonates, etc. A preferred woven fabric from which to form porous layer 66 is commercially available as "Saatifil TM Polyester PES 18-13" from Saati Corp., Stamford, Conn. This material has an average mesh size of about 18 microns and a void volume fraction of about 13 percent. Preferred porous layers would include porous polymer films produced by phase inversion, laser ablation and other well known processes.

The material from which to form porous layer 66 is selected so as to have an appropriate surface energy for the liquid to be dispensed by the applicator. For example, where the liquid to be applied has relatively high surface tension, such as water, the porous layer 66 is made from a material which has relatively high surface energy, such as polyacrylamide. In this way, wetting of the porous layer 66 by the high surface tension liquid is assured. With liquids having relatively low surface tensions, such as isopropyl-alcohol or ethanol, the choice of the material from which to form porous layer 66 is less important, since liquids with low surface tensions will wet porous layers with high or low surface energies. Preferably the porous layer is between about 5 microns (0.2 mil) and 525 microns (20 mil) thick, more preferably between about 12 microns (0.5 mil) and 50 microns (2 mil) thick.

One type of useful porous layer is a novel microstructured isoporous membrane having an array of pores therein, and made by a novel method. These novel membranes comprise a sheet having first and second major faces with at least one array of pores that extend through the entirety of the sheet from the first face to the second face.

The membranes of the invention differ from those previously available in a number of ways including but not limited to the following:

(a) the pores within a given array can exhibit a degree of uniformity of size, shape, and/or orientation that was previously unattainable;

(b) the pores can have desired shapes and sizes and can be arranged in geometries not previously attainable;

(c) the pores can be formed in membranes made of materials in which such pores could not previously be formed;

(d) the membrane can exhibit a degree of side to side uniformity that was previously either not attainable or not readily attainable; and (e) the land areas between pore openings are flat.

As a result of their novel features, membranes of the invention provide unexpected and/or previously unattained advantages and utility.

Figure 7:
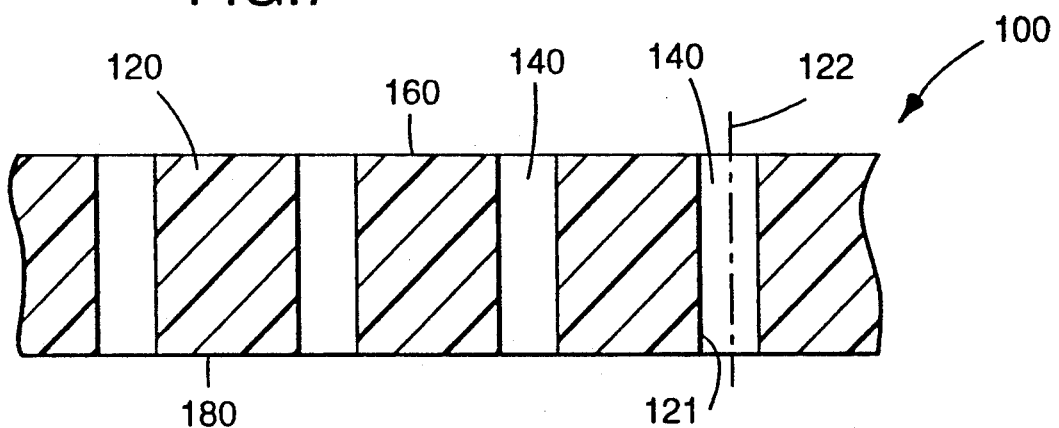
FIG. 7 is a cross sectional view of a portion of one embodiment of a microstructured membrane with orifices of the invention.

FIG. 7 shows an illustrative embodiment of a microstructured membrane of the invention wherein membrane 100 comprises sheet 120 with pores 140 therein. Pores 140 open in first face 160 of sheet 120 and extend through the entirety of sheet 120 to open through second face 180.

An additional feature of some embodiments of these membranes is that, referring to FIG. 7, major portion 121 of the walls of each pore 140 are substantially parallel to longitudinal axis 122 of pore 140. As used herein, "longitudinal axis" refers to the axis of the pore extending through the sheet 120. By "substantially parallel" it is meant that the deviation between the major portion of the wall of each opening and the longitudinal axis is less than about 5 degrees. Accordingly, in these embodiments the pore has a substantially uniform cross-sectional area throughout at least the portion defined by the major portions of its walls. As used herein, "cross-sectional area" refers to the area of a geometric surface on a plane perpendicular to the longitudinal axis of the pore and bounded by the intersection of the plane with the walls of the opening.

In these membranes the major portion, i.e., at least 50 percent and typically preferably at least 75 percent, of the length of the walls of each pore beginning at the edge of the opening in the first face of the sheet and extending through the sheet are substantially straight. Explained in another way, the regions of intersection with the walls or sides of an a pore of any plane parallel to and intersecting the longitudinal axis of the pore are straight lines for at least 50 percent and typically preferably at least 75 percent of the length of the regions of intersection.

These membranes may be made with pores having an average "characteristic dimension" of desired size. As used herein, "characteristic dimension" means the largest cross-sectional dimension of the pore in a plane perpendicular to the longitudinal axis of the pore.

Two or more arrays of pores having different properties of size, shape, orientation or distribution throughout the membrane also may be utilized. An advantage of using the membranes described herein is that the membrane may have, within a given array of pores, a pore size distribution of less than about 10 percent and sometimes less than 5 percent. As used herein, "pore size distribution" means the standard deviation of the average characteristic dimension.

Figure 10:
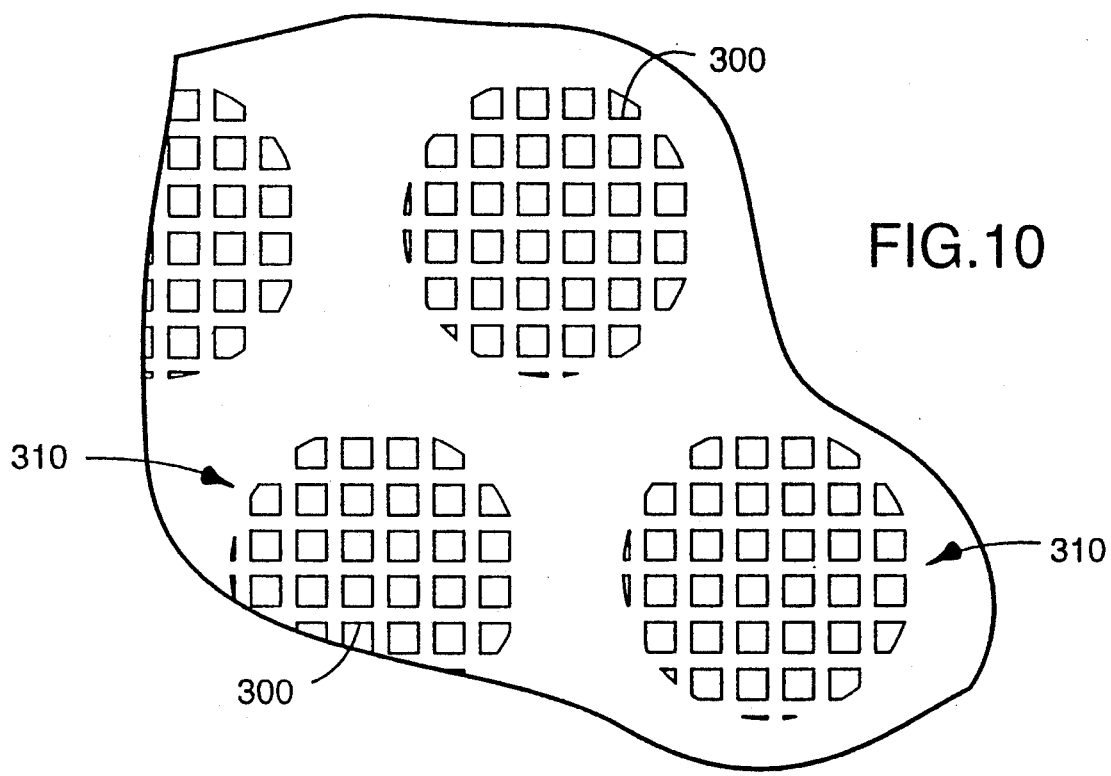
FIG. 10 is a magnified plan view of the membrane fabricated in Example 3, pore sizes not to scale.

The membranes of the invention may be made with pores having a variety of shapes, i.e., cross sectional profile of the pore as the region of a plane perpendicular to longitudinal axis of the pores bounded by the pore walls. For instance, by selection of a suitable mask, pores may have a cross-sectional profile that is circular, ovate, square, rectangular, triangular, some other polygon, or irregular shapes. The orifices or pores may also be provided in a polka dotted pattern with relatively large areas of densely spaced uniform pores separated by other relatively large areas where there are no pores. A membrane with a polka dotted pattern is shown in FIG. 10. Referring to FIG. 10, the average dimension of the pores 300 is preferably between about 5 and 60 microns, most preferably between about 15 and 50 microns. The areas 310 containing the pores preferably have an average dimension of about 1 to 7 mm, more preferably 2 to 6 mm, and are separated by average distances of preferably about 3 to 8 mm, more preferably about 4 to 7 mm.

Membranes useful in the practice of the invention may be made from films of many types including polymeric materials and metals, such as metal foils. A particularly preferred material is polyethylene terephthalate. As discussed below, selection of the film material and selection of the boring means are dependent in part upon one another.

In general, ultraviolet boring techniques, e.g., ablation, may be used with polymeric films that contain unsaturated bonds. Membranes may be made using ultraviolet boring techniques with other polymers by incorporating ultraviolet absorbers therein to render the film ablative. Such absorbers are well known and may be readily selected and used by those with ordinary skill in the art.

Reactive ion etching techniques may also be used to make membranes of the invention from sheets of some types of polymers and metals.

An advantage to using the membranes described herein is that they may be made with pores having very low aspect ratios, e.g., 1:100, or up to very high aspect ratios, e.g., 60:1. As used herein, "aspect ratio" refers to the ratio of (1) the interior length of the longitudinal axis of the pores, i.e., the portion of the longitudinal axis which is within the volume of film vacated during boring of the pores, to (2) the average characteristic dimension of the pores. An advantage of the highly uniform pore size and narrow distribution of pore size which can be achieved in membranes of the invention is that the resultant membranes can exhibit highly uniform characteristics.

Figure 8:
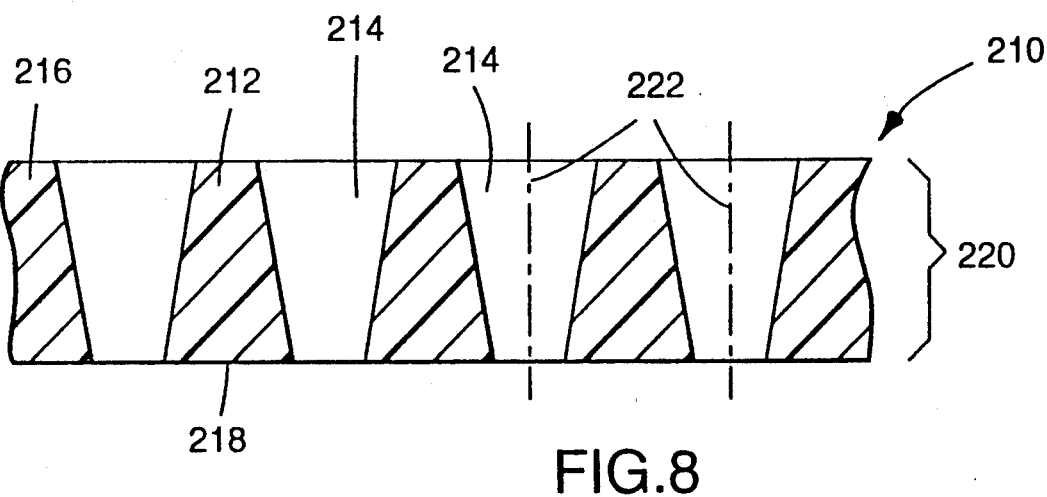
FIG. 8 is a cross sectional view of a portion of another embodiment of a microstructured membrane of the invention.
Figure 9:
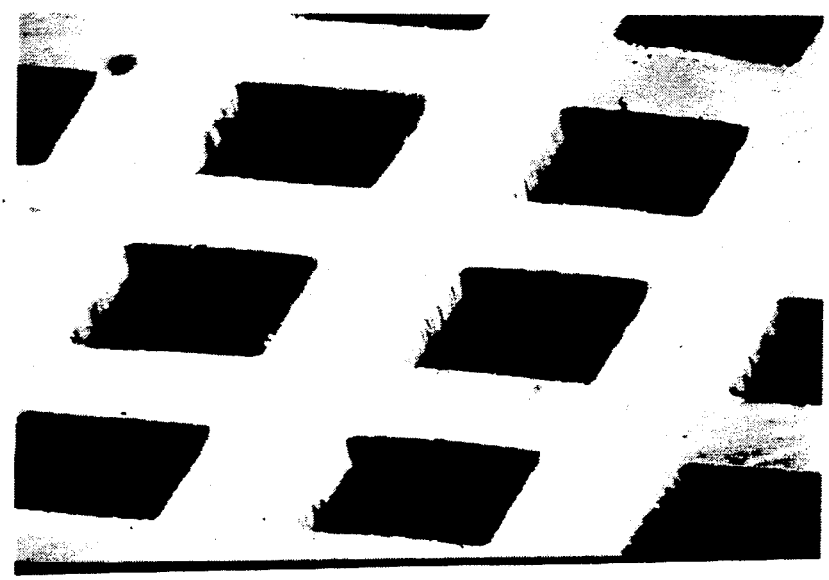
FIG. 9 is a scanning electron microscope photograph representative of the membrane fabricated in Example 1.

In some embodiments, membranes may be made wherein the walls of the pores define frustum-like shapes. In such instances, each pore does not have a uniform cross-sectional area and the major portions of the walls of each pore are not substantially parallel to the pore's longitudinal axis. FIG. 8 illustrates membrane 210 comprising sheet 212 with pores 214 therein extending from first face 216 through second face 218. Major portions 220 of pores 214 are not parallel to each other or to longitudinal axis 222. As with other embodiments, however, at least 50 percent and preferably at least 75 percent of the length of the walls of each pore within a given array are straight. An advantage of such membranes is that they offer greater strength than do membranes with pores with similar minimum cross-sectional areas but having non-linear walls or wherein the dividers between adjacent pores are saddle-shaped. Some embodiments of such pores are sometimes referred to as being "Gaussian-shaped". Membranes with frustum like pores exhibit less tendency to clog when the stream being filtered enters the face of the membrane having the smaller ends of the pores.

In some embodiments, membranes will comprise two or more arrays of different pores as described herein wherein the pores in different arrays have different characteristics. The arrays may be located at separate areas of the membrane or may be partially or totally superimposed.

An advantage of membranes of of the invention is that the portions of the first face between pores, referred to herein as "land areas", and the land areas in the second face are substantially planar or flat. In a tangential flow of fluid across either face of membranes of the invention, the lack of surface saddle-like structures will allow for a better sweep of the fluid across the surface. Furthermore, membranes having saddle-like dividers between pores exhibit reduced flexural strength as compared to membranes of the invention.

In general, the methods for making membranes of the invention comprise:

(a) providing a mask comprising a sheet with an array of apertures therein, the apertures being of the diameter and shape of the desired pores and being arranged in a pattern corresponding to that desired of the pores;

(b) positioning the mask in close proximity to, preferably in intimate contact with, the first face of a film from which the membrane is to be formed; and (c) forming an array of pores simultaneously in the film by application of directional means for boring through the mask; to yield the membrane with the array of pores therein.

Selection of means for boring will be based in part upon the nature of the mask used, the characteristics of the film from which the membrane is being made, and the features desired of the pores. Illustrative examples of means for boring include application of a collimated stream of reactive ions, plasma, or collimated energy beam (e.g., excimer laser or ultraviolet beam). In addition to being highly directional, the means for boring is preferably one which substantially does not deform the sheet outside the area being bored, i.e., one which substantially causes only localized removal of sheet material in the desired location and not in the surrounding land areas. For this reason, conventional chemical etching is typically not desired because it typically does not exhibit the desired directional boring. Preferably, by products produced during boring, e.g., ablation by products, are removed during boring such as by ventilation.

The foam sponge 16 comprises an open cell foam material compatible with the liquid to be dispensed. Suitable open cell foam sponge materials are prepared from thermoplastic materials such as polyethylene and polyurethane. Especially preferred open cell foam materials are prepared from polyurethane thermoplastics.

By utilizing a permanently compression set foam, the wicking and reservoiring properties of the foam sponge can be selected such that the liquid delivered through the porous layer 66 of the metering/bonding insert 72 wets the foam sponge 16 but does not drip from the sponge when the applicator is held with the sponge horizontal. The compression set of the foam sponge can also be selected to affect the coating characteristics of the applicator. The greater the compression set, the greater the amount of liquid that can be absorbed by the sponge material. Preferably, the foam sponge material is compressed by heat and pressure to about 1.5 to 10 times its original density, i.e., the compression set ratio is between about 1.5 and 10. Most preferably, the compression set ratio of the sponge is between about 2 and 4.

The porosity of the foam sponge 16 can also be selected to affect the wetting and coating characteristics of the applicator. Preferably, for surgical prep applications, the porosity of the foam sponge material is between 4 and 40 pores per linear centimeter, more preferably about 35 pores per linear centimeter. A particularly preferred open cell foam sponge material is an elastomeric polyurethane foam having a compression set ratio of between about 2 and 4 and a porosity of about 35 pores per linear centimeter, commercially available from Foamex, LP, East Providence, R.I. as "SIF-2.5-900Z".

The applicator of this invention is useful in dispensing liquids having viscosities at room temperature of less than about 10,000 cps, most preferably less than about 500 cps.

As noted above, the applicator is useful in dispensing antiseptic liquids to cleanse a surgical field prior to surgery. Examples of suitable antiseptic preparations include those described in U.S. Pat. No. 4,584,192 and those described in U.S. Pat. No. 4,542,012, the disclosures of which are incorporated herein by reference. Preferred antiseptic preparations are iodophoric skin tinctures, such as "Duraprep TM Surgical Solution," commercially available from 3M. The antiseptic liquid is delivered to the foam sponge 16 which is gently rubbed over the surgical field to thereby cleanse it. The applicator can be actuated and handled easily without dripping the liquid onto other articles in the vicinity of the surgical field. The dripless feature and the ability to apply a controlled uniform coat allows application of the liquid to only the desired areas of the patient and also allows for quicker and more efficient use of a surgical facility due to elimination of the time needed to clean the facility of antiseptic prep that dripped and flowed off of the patient.

The invention is further illustrated by the following non limiting examples.

EXAMPLE 1

Preparation of a Microstructured Porous Layer

A stainless steel mask with uniformly distributed square apertures was placed in contact with a 25 micron (1 mil) thick poly(ethylene terephthalate) (i.e., "PET"), MYLAR TM film (from E.I. duPont de Nemours). The sides of the apertures were 15 microns in length with, according to the manufacturer, a standard deviation of about 10 percent and about 35 percent of the mask was open area.

The beam from a krypton/fluorine ("KrF") excimer laser producing 248 nanometer ("nm") radiation at a pulse frequency of 40 Hertz ("Hz") and pulse duration of 27 nanoseconds was projected through an iris and a series of lenses onto the mask. The iris was located about 30.5 centimeters ("cm") from the laser window and a few cm from the first lens. The lenses included (1) a 106.7 cm focal length converging lens located about 108 cm (42.5 inches) from the PET film plane, (2) a 20.3 cm focal length diverging lens located about 73 cm (28¾ inches) from the PET film plane, and (3) a 3.4 cm focal length cylindrical lens located about 4 cm (1.5 inches) from the film. These lenses are commercially available from ESCO Products Company and are made of CORNING TM 7490-UV, a material transparent to light at a wavelength of 248 nm, with AR-MgF$_2$ antireflective coatings.

Ablation was accomplished by shadowing the mask pattern onto the PET film. The intensity of the laser radiation incident to the surface of the film was about 200 millijoules per centimeter$^2$ ("mJ/cm$^2$") with a beam shape at the surface of a rectangle about 3 millimeters (120 mils) wide and 15.2 cm (6 inches) long. The mask and PET film were moved in register across the middle 10.2 cm (4 inches) of the beam at a rate of about 0.25 cm/minute.

Scanning the mask/film combination yielded a 10.2 cm wide PET membrane with pores penetrating through the membrane. The axes of these pores were parallel to one another and perpendicular to the membrane surfaces.

Surgical Prep Applicator

The PET membrane was used as the porous layer ampoule was filled with 26 milliliters of "Duraprep TM Surgical Solution". In two trials, the time required for the applicator to dispense 13 of the 26 milliliters of solution after breaking the ampoule was measured. Times of 15 and 16 seconds were observed.

In comparison, liquid dispensers as disclosed in U.S. Pat. No. 4,925,327 having substantially equal size as those above were observed to take from 15 to 60 seconds to dispense an equal amount of the same fluid.

EXAMPLE 2

A 9.6 millimeter thick sample of open cell polyurethane foam commercially available as "SIF-2-900Z" from Foamex, LP, of East Providence, R.I., was subjected to the following treatment. The surface of the foam was skinned by passing the foam under a heated (200° C.) bar. One surface of the foam contacted the heated bar and was melted. When the surface was melted, the foam cell structure collapsed creating a skin approximately 50 to 100 microns thick. This skin layer was subjected to the laser treatment using the mask and laser apparatus detailed in Example 1, except that the sides of the apertures in the mask were 53 microns in length. The foam was then used in an applicator for "Duraprep TM Surgical Solution" substantially as depicted in FIG. 2, except that no separate porous layer other than that integral to the modified foam was employed. The time required for the applicator to dispense 13 mls of fluid when tested as described in Example 1 was 15 seconds.

EXAMPLE 3

The superimposed pattern of two stainless steel masks was simultaneously replicated onto a 25 micron (1 mil) thick poly(ethylene terephthalate) (i.e., "PET"), MYLAR TM film (from E.I. duPont de Nemours). The first mask had square apertures uniformly distributed in a square array wherein the sides of the apertures were 38 microns in length with, according to the manufacturer, a standard deviation of about 10 percent and about 36 percent of the mask was open area. The first mask was placed in contact with the PET film. The second mask had round apertures of 4500 microns in diameter distributed in a center filled hexagonal array so sized that about 46 percent of the mask was open area. The second mask was placed over the exposed surface of the first mask. About 16 percent of the pattern exposed by the combined array was open area.

The beam from a krypton/fluorine ("KrF") excimer laser described in Example 1 was used to ablate by shadowing the mask pattern onto the PET film, as described in Example 1.

Scanning the mask/film combination yielded a 10.2 cm wide PET membrane with pores penetrating through the membrane. The axes of these pores were parallel to one another and perpendicular to the membrane surfaces. Where the edges of the round apertures of the second mask happened to overlap the edges of the square apertures of the first mask, some non square openings in the PET membrane were created.

The membrane was then used as the flexible, porous layer 66 in an applicator for "Duraprep TM Surgical Solution", substantially as depicted in FIG. 2. The average time required for 13 mls of fluid to flow through the foam sponge of the applicator was tested as described in Example 2, and was 12.6 seconds.

Although specific embodiments of the invention have been described herein, it is not intended to limit the invention solely thereto, but to include all of the obvious variations and modifications within the spirit and scope of the appended claims.

We claim:

1. An article useful as a dispenser for the application of a liquid to a surface, comprising
    (a) a hollow elongate member having a first major orifice at one end thereof;
    (b) a flexible, porous layer disposed over said first major orifice having at least one array of pores extending therein, each array of pores having an average pore size of between about 1 and 100 microns and a distribution of pore sizes of less than about 30 percent of the average pore size;
    (c) a layer of sponge material disposed over the exterior surface of said porous layer; and
    (d) means of maintaining atmospheric pressure within said hollow elongate member while the liquid to be applied by said applicator is being dispensed.

2. The article of claim 1 wherein said flexible porous layer is selected from the group consisting of woven fabric, knit fabric, nonwoven fabric, porous plastic film, porous plastic membrane, and porous metal foil.

3. The article of claim 2 wherein said porous layer is made from a material selected from the group consisting of: polyvinyls, polyynes, polyenes, polydienes, polyesters, polyurethanes, polyamides, polyimides, polyethers, polycarbonates, polyacrylamides and polyacrylonitriles.

4. The article of claim 1 wherein said flexible porous layer is capable of being wrapped around a 1 millimeter diameter mandrel without breaking.

5. The article of claim 1 wherein the void volume fraction of said porous layer is between about 0.5 and 50 percent.

6. The article of claim 1 wherein said flexible porous layer is capable of limiting liquid flow therethrough to between about 0.1 and 15 milliliters/second.

7. The article of claim 1 wherein said flexible porous layer is a microstructured membrane comprising a sheet with at least one array of pores extending through said sheet, each array of pores having a pore size distribution of less than about 10 percent.

8. The article of claim 7 wherein said sheet comprises at least a second array of pores extending through said sheet, the pores in the second array having a pore size distribution of less than about 10 percent, and wherein at least one of said average pore size, said pore size distribution, or said shape of the pores of said second array is different from said pore size, said pore size distribution, or said shape of the pores of said first array.

9. The article of claim 1 wherein the pores in the layer are uniformly distributed throughout the porous layer.

10. The article or claim 1 wherein the pores are distributed throughout the porous layer in a polka-dotted pattern.

11. The article of claim 1 wherein said porous layer is about 5 to 525 microns thick.

12. The article of claim 1 wherein said means of maintaining atmospheric pressure comprises a cap with an air vent placed over a second major orifice in said hollow elongate member, said second major orifice being on the opposite end of the hollow elongate member from the first major orifice.

* * * * *